(12) United States Patent
Chen

(10) Patent No.: US 8,262,887 B2
(45) Date of Patent: Sep. 11, 2012

(54) METHOD FOR INCREASING MEASUREMENT PRECISION OF TWO-DIMENSIONAL PROTEIN

(76) Inventor: Han-Min Chen, Taipei (TW)

(*) Notice: Subject to any disclaimer, the term of this patent is extended or adjusted under 35 U.S.C. 154(b) by 15 days.

(21) Appl. No.: 12/759,711

(22) Filed: Apr. 14, 2010

(65) Prior Publication Data

US 2011/0253536 A1    Oct. 20, 2011

(51) Int. Cl.
*G01N 27/447* (2006.01)
(52) U.S. Cl. ........................................ 204/548
(58) Field of Classification Search ........... 204/450–470
See application file for complete search history.

(56) References Cited

U.S. PATENT DOCUMENTS 5,286,356 A * 2/1994 Jones et al. ............... 204/452

* cited by examiner

*Primary Examiner* — J. Christopher Ball

(57) ABSTRACT

A method for increasing measurement precision of two-dimensional protein electrophoresis is provided, in which the electrical conductivity of a protein sample under test is measured for calculating the electrical energy required to enable salt and protein focusing. The method is characterized by a set of equations for calculating the electrical energy required respectively for protein focusing and for electrophoresis of salts in the protein sample, wherein the calculation is based on the electrical conductivity of the salts, the protein weight, a pH-gradient gel strip length, and a pH range. Thus, different protein samples can be supplied with the appropriate amounts of electrical energy for isoelectric focusing, so as to produce the optimal protein focusing effects and ensure that the focusing of protein in a gel will not be adversely affected by an otherwise insufficient or excessive supply of electrical energy.

7 Claims, 1 Drawing Sheet

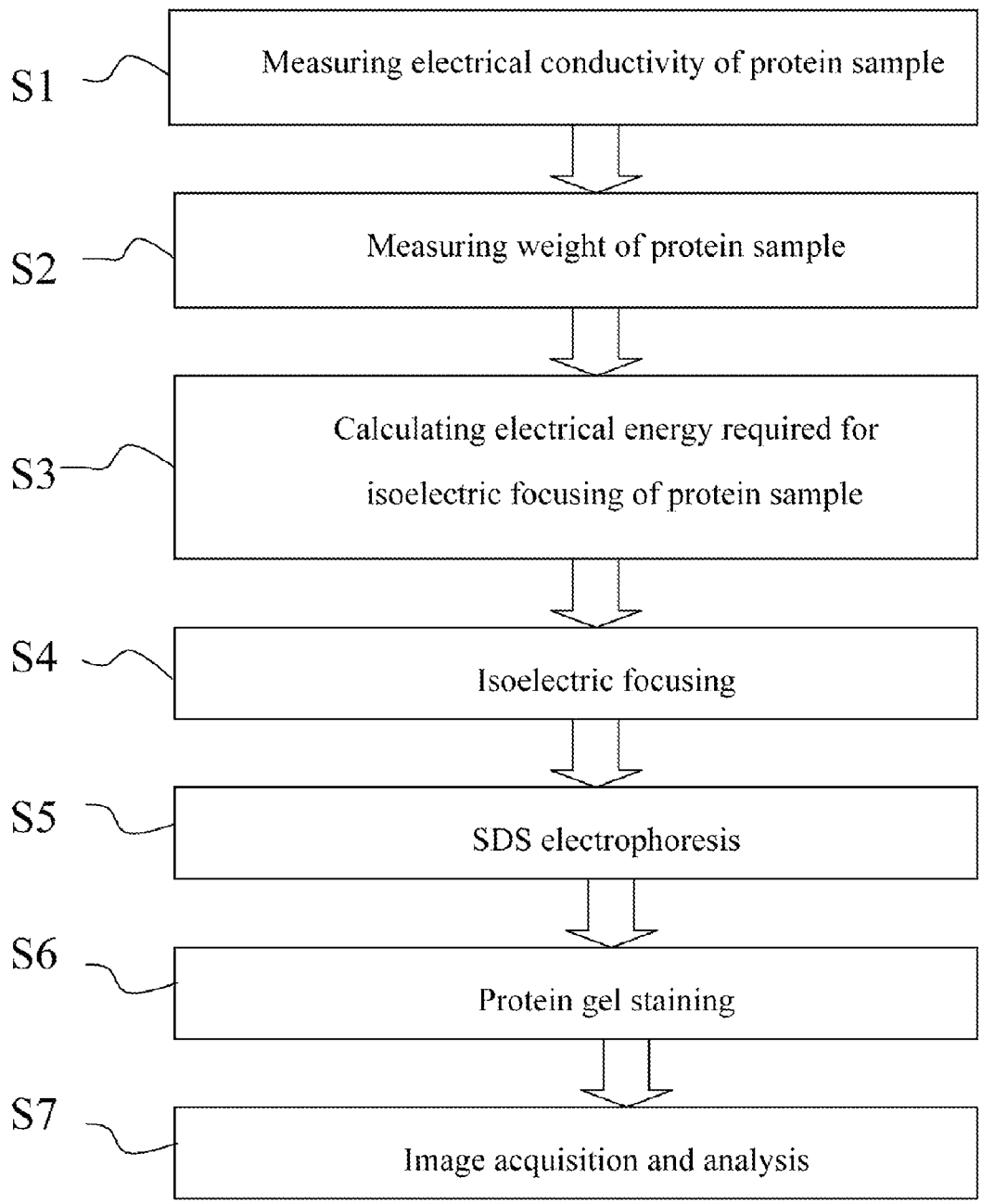

METHOD FOR INCREASING MEASUREMENT PRECISION OF TWO-DIMENSIONAL PROTEIN

BACKGROUND OF THE INVENTION

1. Technical Field

The present invention relates to a method for increasing the precision of two-dimensional protein electrophoresis. More particularly, the present invention relates to a method which includes measuring the electrical conductivity of a protein sample under test, assessing the salt content of the protein sample according to the measurement result, and using a set of equations to calculate the electrical energy required respectively for protein focusing and for electrophoresis of salts in the protein sample.

2. Description of Related Art

From the 1980s onward, bioengineering has contributed significantly to the advancement of scientific techniques. In particular, electrophoretic separation, on which many important researches depend, has been an almost indispensable experimental approach in chemistry, molecular biology, and the related industries. As the net charge on a protein molecule is determined by the pH level of the surroundings, electrophoretic separation must be conducted in a special medium, typically a semi-solid gel such as polyacrylamide gel, as the matrix for electrophoresis. Nowadays, electrophoresis has evolved into a number of different techniques, namely SDS-polyacrylamide gel electrophoresis (SDS-PAGE), isoelectric focusing (IEF), two-dimensional electrophoresis, protein transfer, and so on.

In two-dimensional electrophoresis, the separation of molecules is carried out in two electrophoresis directions. More specifically, isoelectric focusing is applied to the first direction while SDS electrophoresis, which separates molecules by molecular weight, is applied to the second direction. The principles of isoelectric focusing are briefly stated as follows. To begin with, a gel containing an amphoteric electrolyte is used as the medium for electrophoresis of a protein sample. When an electrical field is applied to the gel, the amphoteric electrolyte forms a pH gradient in the gel. Under the action of the electrical field, the protein in the sample moves to a position where the pH value is equal to its isoelectric point (pI), i.e., pH=pI. Consequently, the net charge on the protein becomes zero, and the protein is focused (i.e., remains stationary) at that particular position and thus separated from the other ingredients of the sample. On the other hand, SDS-PAGE is performed in a gel added with SDS. SDS is a surfactant capable of destroying the configuration of protein molecules and evenly coating the surfaces of protein molecules with a layer of negatively charged SDS molecules. Hence, regardless of whether the protein molecules are positively or negatively charged in the first place, the SDS coating will make all the protein molecules migrate toward the positive electrode, during which process the migration speed is in inverse proportion to molecular weight. Therefore, SDS-PAGE can be used to measure the molecular weight of protein and effectuate two-dimensional protein separation in a gel.

After a biological sample under test is dissolved in a gel, the gel may contain several kinds of salts in addition to protein molecules. Due to the fact that salts have electrolytic properties, a portion of the voltage, or electrical energy, applied to the gel for protein electrophoresis is used instead to drive the electrolytic salts to migrate. As the salt content of a sample is related to the biological feature of the sample as well as the test itself and cannot be accurately evaluated, the electrical energy consumed by the salts during the isoelectric focusing process of a two-dimensional electrophoresis is hardly assessable, and so is the electrical energy used for electrophoresis of protein molecules in the sample. If isoelectric focusing is carried out with an insufficient supply of electrical energy to the protein molecules, the protein focusing effects on the isoelectric focusing gel strip will be poor, and under-focusing is likely to occur. However, an excessive supply of electrical energy may cause the protein molecules to migrate off the gel strip, thus resulting in over-focusing. Therefore, it has been a standard laboratory procedure to remove salts from a protein sample by protein precipitation and adequate rinsing, which nevertheless may lead to loss of many important proteins. Moreover, certain protein samples simply cannot precipitate effectively during the process.

The aforesaid problems have yet to be solved by persons skilled in the art.

BRIEF SUMMARY OF THE INVENTION

So far no methods have been proposed for measuring the efficiency of isoelectric focusing and thereby increasing the precision of two-dimensional protein electrophoresis. The main reasons for the lack of such methods lie in the fact that the protein to be tested in two-dimensional protein electrophoresis has a relatively small volume, and that the content of salts in a protein sample is difficult to measure due to the complicated compositions of the salts. Another reason is the lack of methods for quantitatively calculating the electrical energy consumed respectively by protein and salts in an isoelectric focusing experiment, such that there is no suitable logic by which an experiment operator can assess this electrical energy beforehand in order to obtain the desired protein focusing results. However, since there is a linear relationship between the electrical conductivity and salt content of an aqueous solution, the salt content of a protein sample in two-dimensional electrophoresis must also have certain relationship with the electrical conductivity of the sample. Therefore, the salt content of a protein sample should be evaluable by measuring the electrical conductivity of the sample.

In view of the aforementioned deficiencies of the prior art, the inventor of the present invention proposes a method for increasing the precision of isoelectric focusing and thereby achieving the following objects.

The first object of the present invention is to measure the electrical conductivity of a protein sample to be tested in two-dimensional electrophoresis, so as to determine the salt content of the protein sample and thereby calculate the electrical energy required by salts in the protein sample during isoelectric focusing.

The second object of the present invention is to provide a set of equations for calculating the total electrical energy required for isoelectric focusing, wherein the parameters of the equations include the salt content of the sample (represented by electrical conductivity), the protein content of the sample (expressed by weight), a pH-gradient gel strip length, and a pH range. The equations can be used to calculate the electrical energy required respectively for focusing protein in the sample and for causing salts in the sample to migrate. The calculation results are summed up to precisely determine the total electrical energy required for performing isoelectric focusing on the sample. Thus, not only is the precision of two-dimensional protein electrophoresis enhanced, but also the undesirable protein focusing effects which may otherwise result from an insufficient or excessive supply of electric energy in an isoelectric focusing experiment are prevented.

BRIEF DESCRIPTION OF THE SEVERAL VIEWS OF THE DRAWINGS

The present invention is described in detail hereinafter with reference to a preferred embodiment configured for achieving the foregoing objects and effects. It is intended that a person of ordinary skill in the art will be enabled to implement the technical contents disclosed herein by reviewing the following description in conjunction with the accompanying drawing, in which:

FIG. 1 is the flowchart of a method according to an embodiment of the present invention.

DETAILED DESCRIPTION OF THE INVENTION

Please refer to FIG. 1 for the flowchart of a method for increasing the precision of two-dimensional protein electrophoresis according to an embodiment of the present invention. More particularly, the method involves measuring the electrical conductivity of a protein sample and calculating the electrical energy required for focusing protein as well as salts in the protein sample. As shown in FIG. 1, the method includes the following steps:

(1) Measurement of the Electrical Conductivity $S_{Exp}$ a Protein Sample

A handheld electrical conductivity meter, such as OAKTON ECTestr 11+ (Oakton Instruments, Vernon Hills, Ill., USA) is used to take a protein sample of 250 μL at 4° C. The protein sample is placed at the reading end of the electrical conductivity meter so as to measure the electrical conductivity of the sample (in the unit of μS/cm, S: siemens). The final result is the average of three measurements.

(2) Measurement of the Weight $M_{Exp}$ of the Protein Sample (3) Calculation of the Electrical Energy Required for Isoelectric Focusing of the Protein Sample.

The calculation is performed by substituting system parameters into the following set of equations. Assuming the electrical conductivity of salts in a rehydration gel solution of 125 μL is 31 μS; the electrical conductivity of a gel solution containing no protein is 25 μS; the weight of a reference protein $M_{ref}$ is 50 μg; a reference pH-gradient gel strip length is 7 cm; a reference pH range is 3-10; the electrical energy $Vh_{salt\_ref}$ for enabling electrophoresis of a reference salt is 200 Vh, as obtained by reference to experiment results; the electrical energy $Vh_{protein\_ref}$ for enabling focusing of a reference protein is 1050 Vh, as obtained by reference to experiment results; the weight of the protein sample is measured as 50 μg; the actual pH-gradient gel strip length available for use which is 1 cm shorter than a reference pH-gradient gel strip length is 6 cm; the pH-gradient gel strip length used is 13 cm; and the actual pH range is 4-7, the electrical conductivity of the salts in this protein sample is 31 μS also, then the total electrical energy required for protein focusing is 5833 Vh.

$$Vh_{protein\_exp} = Vh_{protein\_ref} \times \frac{M_{exp}}{M_{ref}} \times \frac{\text{strip } length_{exp}}{\text{strip } length_{ref}} \times \frac{\text{pH } range_{ref}}{\text{pH } range_{exp}} \quad (c1)$$

$$= 1050Vh \times (50\mu g / 50\mu g) \times (12cm / 6cm) \times$$
$$(10 - 3)/(7 - 4)$$
$$= 4900Vh$$

$$Vh_{salt\_exp} = Vh_{salt\_ref} \times \frac{S_{exp} - S_{blank}}{S_{ref} - S_{blank}} \times \frac{\text{strip } length_{exp}}{\text{strip } length_{ref}} \times \frac{\text{pH } range_{ref}}{\text{pH } range_{exp}} \quad (c2)$$

$$= 200Vh \times (31\mu S - 25\mu S)/(31\mu S - 25\mu S) \times (12cm/6cm) \times$$
$$(10 - 3)/(7 - 4)$$
$$= 933Vh$$

$$Vh_{total} = Vh_{protein} + Vh_{salt} = 4900Vh + 933Vh = 5833Vh \quad (c3)$$

(4) Isoelectric Focusing

Protein particles are washed and dissolved in a rehydration buffer solution which contains 8M of urea, 2% of propane sulfonic acid, 0.5% of gradient buffer solution, and 18 mM of dithiothreitol. The protein sample is put in an electrophoresis system (IPGphor II system, GE Healthcare BioSciences) and maintained at 20° C. for 18 to 24 hours so as to be dissolved in pH-gradient gel strips (GE Healthcare BioSciences, Piscataway, N.J., USA) of different lengths and different pH ranges. The maximum focusing current applied is 100 Ma/strip.

(5) SDS Electrophoresis

The pH-gradient gel is allowed to reach equilibrium in an SDS buffer solution (75 mM of tris(hydroxymethyl)aminomethane, 6M of urea, 30% of glycerin, 2% of SDS, and 0.01% of bromophenol blue, with a pH value of 8.8). Then, 1% of dithiothreitol or 2.5% of iodoacetamide is added to the solution to denature the protein. When equilibrium is reached again, SDS electrophoresis is carried out by 12.5% SDS-PAGE in the SE-260, SE-600, or Daltsix electrophoresis system (GE Healthcare BioSciences).

(6) Protein Gel Staining

Imidazole-zinc reverse staining is performed in a reagent box, such as VisPro 5-Min Protein Stain Kit (Visual Protein, Taipei, Taiwan). After electrophoresis, the gel is promptly rinsed with distilled water and moved into the box. Following that, a sensitization solvent is added into the box, and the box is placed on a vibrator and agitated for five minutes. Afterward, the gel is washed with distilled water, added with a culture solution, and then immersed in a large quantity of distilled water to stop development. The gel thus modified turns into a white background while protein spots become opaque. The stained gel can be stored in distilled water.

(7) Image Acquisition and Analysis

All the modified gels are scanned by an optical flatbed scanner with a transparent unit, in TIFF format and with a solution of 200 dpi. The stained spots on the gels are recorded as reversed images for better image quality. For image analysis, ImageMaster 2D Platinum software version 5.0 (GE Healthcare BioSciences) is used to count the number of protein spots.

While the present invention has been described with reference to the preferred embodiment, it is understood that the embodiment is not intended to limit the scope of the present invention. The scope of the present invention is defined only by the appended claims.

What is claimed is:

1. A method for increasing measurement precision of two-dimensional protein electrophoresis, essentially comprising steps of:
   (a) measuring a weight $M_{exp}$ of a protein sample;
   (b) measuring an electrical conductivity $S_{exp}$ of salts in the protein sample;

(c) providing a set of equations for calculating a total electrical energy to be supplied to the protein sample, the set of equations including:

$$Vh_{protein\_exp} = Vh_{protein\_ref} \times \frac{M_{exp}}{M_{ref}} \times \frac{\text{strip length}_{exp}}{\text{strip length}_{ref}} \times \frac{\text{pH range}_{ref}}{\text{pH range}_{exp}}; \quad (c1)$$

$$Vh_{salt\_exp} = Vh_{salt\_ref} \times \frac{S_{exp} - S_{blank}}{S_{ref} - S_{blank}} \times \frac{\text{strip length}_{exp}}{\text{strip length}_{ref}} \times \frac{\text{pH range}_{ref}}{\text{pH range}_{exp}}; \quad (c2)$$

and $$Vh_{total} = Vh_{protein} + Vh_{salt}; \quad (c3)$$

$$Vh_{total\_exp} = Vh_{protein\_exp} + Vh_{salt\_exp} \quad (c4)$$

where $Vh_{protein\_exp}$ is an electrical energy for enabling protein focusing, to be determined by the equation (c1); $Vh_{salt\_exp}$ is an electrical energy for enabling salt electrophoresis, to be determined by the equation (c2); $Vh_{protein\_ref}$ is an electrical energy for enabling focusing of a reference protein; $Vh_{salt\_ref}$ is an electrical energy for enabling electrophoresis of a reference salt; $M_{ref}$ and $M_{exp}$ are a weight of a reference protein and the weight of the protein sample, respectively; $S_{blank}$, $S_{ref}$, and $S_{exp}$ are an electrical conductivity of a gel solution containing no protein, an electrical conductivity of the reference salt, and the electrical conductivity of the salts in the protein sample, respectively; strip length$_{ref}$ and strip length$_{exp}$ are a reference pH-gradient gel strip length and an actual pH-gradient gel strip length, respectively; pH range$_{ref}$ and pH range$_{exp}$ are a reference pH range and an actual pH range, respectively; and $Vh_{total}$, $Vh_{protein}$, and $Vh_{salt}$ are the total electrical energy, an electrical energy for enabling protein focusing, and an electrical energy for enabling salt electrophoresis, respectively; and (d) substituting the electrical conductivity of the salts in the protein sample, the weight of the protein sample, the actual pH-gradient gel strip length, and the actual pH range into the set of equations so as to determine the total electrical energy for enabling protein focusing and achieving optimal protein focusing effects.

2. The method of claim 1, wherein the total electrical energy for achieving the optimal protein focusing effects is a sum of the electrical energy calculated from the equation (c2) for enabling electrophoresis of the salts in the protein sample and the electrical energy calculated from the equation (c1) for enabling focusing of protein in the protein sample.

3. The method of claim 1, wherein the total electrical energy for achieving the optimal protein focusing effects is positively correlated to the weight of the protein sample.

4. The method of claim 1, wherein the total electrical energy for achieving the optimal protein focusing effects is positively correlated to the electrical conductivity of the salts in the protein sample.

5. The method of claim 1, wherein the longer the actual pH-gradient gel strip length is, the more electrical energy is required for moving the salts and protein in the protein sample to respective destinations.

6. The method of claim 1, wherein the narrower the actual pH range is, the more electrical energy is required for moving the salts and protein in the protein sample to respective destinations.

7. The method of claim 1, wherein the actual pH-gradient gel strip length available for use is 1 cm shorter than an original pH-gradient gel strip length.

* * * * *